US00PP09280P

United States Patent [19]

Olesen et al.

[11] Patent Number: Plant 9,280

[45] Date of Patent: Sep. 12, 1995

[54] MINIATURE ROSE PLANT NAMED 'POULBIAN'

[75] Inventors: Mogens N. Olesen; Pernille Olesen, both of Fredensborg, Denmark

[73] Assignee: Beer Creek Gardens, Inc., Medford, Oreg.

[21] Appl. No.: 310,257

[22] Filed: Sep. 21, 1994

[51] Int. Cl.[6] ..... A01H 5/00

[52] U.S. Cl. ..... Plt./8.1

[58] Field of Search ..... Plt. 8.1, 7.1

[56] References Cited

U.S. PATENT DOCUMENTS

P.P. 8,941 10/1994 Olesen et al. ..... Plt./8.1

*Primary Examiner*—Howard J. Locker

*Attorney, Agent, or Firm*—Klarquist Sparkman Campbell Leigh & Whinston

[57] ABSTRACT

A miniature rose plant having attractive white flowers presented in clusters, a very long shelf life, ease of propagation from softwood cuttings, strong, vigorous, upright, well branched, but compact growth, and dark green, glossy, disease resistant foliage.

1 Drawing Sheet

1

The present invention relates to a new and distinct variety of rose plant of the miniature class which was originated by us by crossing two unnamed seedlings.

The primary objective of this breeding was to produce a new rose variety having the strong upright but compact plant habit that is suitable for 10 cm pot plants, combined with ease of propagation from softwood cuttings, very long shelf life and a good display of white flowers. This objective was substantially achieved, along with other desirable improvements, as evidenced by the following unique combination of characteristics that are outstanding in the new variety and that distinguish it from its parents, as well as from all other varieties of which we are aware:

1. Attractive white flowers presented in clusters;
2. A long shelf life;
3. Ease of propagation from softwood cuttings;
4. Strong, vigorous, but compact growth; and
5. Dark green, glossy, disease resistant foliage.

Asexual reproduction of this new variety by softwood cuttings, as performed at Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rose hybrida.*

*Commercial.*—Miniature.

2

FLOWER

Observations made from specimens grown in a greenhouse environment at Fredensborg, Denmark, and Somis, Calif.

Blooming habit: Continuous.

Bud:

*Size.*—½ inch long when the petals start to unfurl.

*Form.*—The bud form is short, blunt, topped.

*Color.*—When sepals first divide, bud color is White Group 155B. When half blown, the upper sides of the petals are White Group 155B; and the lower sides of the petals are White Group 155B.

*Sepals.*—Color: Green Group 138B. Surface texture: Covered in fine hairs. There are three lightly to normally appendaged sepals. There are two appendaged sepals with hairy edges.

*Receptacle.*—Color: Green Group 137C. Shape: Funnel. Size: Small (⅛ inch×⅛ inch). Surface: Smooth.

*Peduncle.*—Length: Medium (1½ inches). Surface: Smooth. Color: Bronzy when young, but turning green quickly. Strength: Stiff, erect.

Bloom:

*Size.*—Small. Average open size is 1¼ inches.

*Borne.*—Singly and several together, in clusters of 3 to 5 flowers. If in clusters: Rounded to flat.

*Stems.*—Medium. Average length is about 5 inches to 6 inches.

*Form.*—When first open: High centered. Permanence: Flattens, outer petals curl back, quill fashion.

*Petalage.*—Number of petals under normal conditions: 25 to 40.

*Color.*—The upper side of the petals is White Group 155B. The reverse side of the petals is White Group 155B. The color of the base of petals is White Group 155B. The major color on the upper side is WHite Group 155B.

*Variegations.*—None.

*Discoloration.*—The general tonality at the end of the first day: No change. At the end of the third day: No change.

*Fragrance.*—Slight.

Petals:

*Texture.*—Thin.

*Shape.*—Oval.

*Form.*—Tips slightly recurved, edges slightly quilled.

*Arrangement.*—Imbricated, with a few small petaloids in the center.

*Persistence.*—Drop off cleanly.

*Lastingness.*—On the plant: Very long (15 to 18 days). As a cut flower: Not tested.

Reproductive parts:

*Anthers.*—Size: Medium. Quantity: Many. Color: Whitish yellow. Arrangement: Regular around styles.

*Filaments.*—Color: Yellow.

*Pollen.*—Color: Yellow.

*Styles.*—Color: Greenish yellow.

*Stigmas.*—Color: Greenish white.

Form: Shrub.

Growth: Vigorous, dwarf, upright, branching, compact. When grown as a 10 cm pot plant, the height of the plant itself is 6 inches to 7 inches.

Foliage: Number of leaflets on normal mid-stem leaves:

*Size.*—Small.

*Quantity.*—Abundant.

*Color.*—New foliage: Green Group 137C. Old foliage: Green Group 139A.

Leaflets:

*Shape.*—Pointed oval.

*Texture.*—Upper side: Glossy.

*Edge.*—Serrated.

*Serration.*—Single, small.

*Petiole rachis.*—Color: Green.

*Petiole underside.*—Smooth, with occasional prickles.

*Stipules.*—Medium, serrated.

*Disease resistance.*—Resistant to mildew and blackspot under normal growing conditions at Fredensborg, Denmark, and resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Red.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its attractive white flowers presented in clusters, a very long shelf life, ease of propagation from softwood cuttings, strong, vigorous, upright, well branched, but compact growth, and dark green, glossy disease resistant foliage.

* * * * *

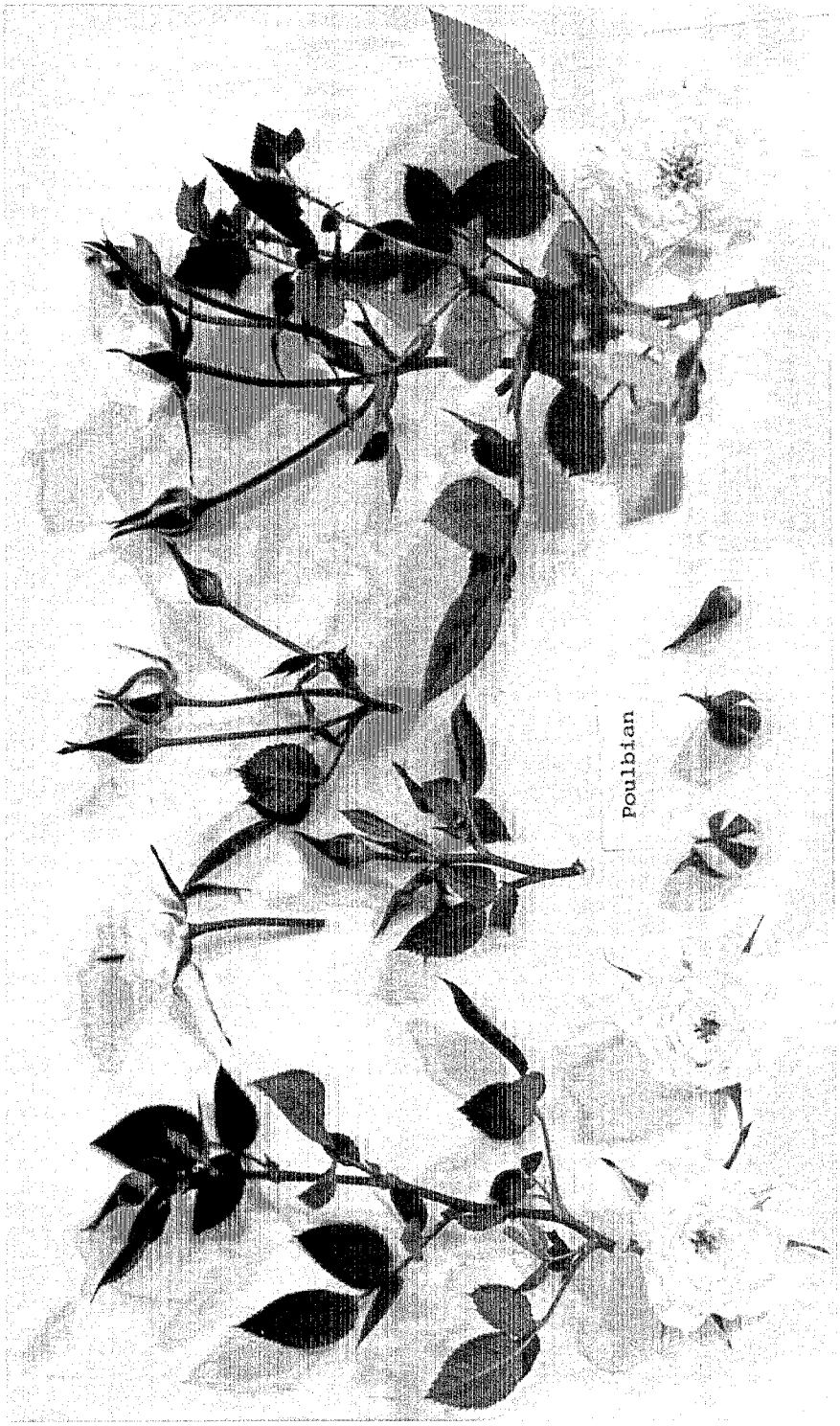
Poulbian

UNITED STATES PATENT AND TRADEMARK OFFICE

CERTIFICATE OF CORRECTION

PATENT NO. : PP 9,280

DATED : September 12, 1995

INVENTOR(S) : Mogens N. Olesen et al.

It is certified that error appears in the above-indentified patent and that said Letters Patent is hereby corrected as shown below:

Column 2, line 19, "two appendaged" should read --two unappendaged--.

Column 2, line 41, "WHite" should read --white--.

Column 3, line 25, "leaves: " should read --leaves: 5--.

Signed and Sealed this

Third Day of September, 1996

*Attest:*

*Attesting Officer*

BRUCE LEHMAN

*Commissioner of Patents and Trademarks*